(12) United States Patent
Lindgren

(10) Patent No.: US 8,718,767 B2
(45) Date of Patent: May 6, 2014

(54) CARDIAC STIMULATING DEVICE

(75) Inventor: Anders Lindgren, Taby (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 13/509,548

(22) PCT Filed: Dec. 18, 2009

(86) PCT No.: PCT/SE2009/051460
§ 371 (c)(1),
(2), (4) Date: May 11, 2012

(87) PCT Pub. No.: WO2011/075025
PCT Pub. Date: Jun. 23, 2011

(65) Prior Publication Data
US 2012/0245650 A1    Sep. 27, 2012

(51) Int. Cl.
*A61N 1/00* (2006.01)
(52) U.S. Cl.
USPC .................. 607/25; 607/5; 607/9; 607/18
(58) Field of Classification Search
USPC ............................................ 607/5, 9, 18, 25
See application file for complete search history.

(56) References Cited

U.S. PATENT DOCUMENTS

| | | | |
|---|---|---|---|
| 4,892,102 A | 1/1990 | Astrinsky | |
| 5,921,923 A | 7/1999 | Kuck et al. | |
| 6,278,894 B1 | 8/2001 | Salo et al. | |
| 2004/0158292 A1 * | 8/2004 | Sheldon et al. | 607/9 |
| 2008/0027494 A1 | 1/2008 | Sheldon et al. | |
| 2008/0046019 A1 | 2/2008 | Sathaye et al. | |
| 2008/0125824 A1 | 5/2008 | Sauer et al. | |
| 2009/0005832 A1 | 1/2009 | Zhu et al. | |

FOREIGN PATENT DOCUMENTS

WO    2008105692 A1    9/2008

OTHER PUBLICATIONS

International Search Report—Int'l App. No. PCT/SE2009/051460; Int'l Filing Date: Dec. 18, 2009.
Written Opinion of the Int'l Searching Authority—Int'l App. No. PCT/SE2009/051460; Int'l Filing Date: Dec. 18, 2009.
Sweeney, Michael O. MD et al., "Ventricular fibrillation induced by double premature ventricular pacing stimuli in a dual-chamber pacemaker with AutoCapture," Heart Rhythm. 2009;6:429-432.

* cited by examiner

*Primary Examiner* — Niketa Patel
*Assistant Examiner* — Lindsey G Hankins

(57) ABSTRACT

An implantable medical device, IMD, comprises atrial and ventricular sensing units for sensing atrial or ventricular electric events. The IMD also comprises atrial and ventricular pulse generators for generating atrial or ventricular pacing pulses. The ventricular sensing unit is connectable to a multi-electrode lead to individually sense electric events in a ventricle using multiple electrode pairs implanted at different ventricular sites. A controller blanks the ventricular sensing unit during a blanking period following delivery of an atrial stimulating pulse by the atrial pulse generator and activates the ventricular sensing unit at the expiry of the blanking period. Due to the lower propagation speed of PVC depolarization waves and the multi-site sensing, a PVC depolarization wave initiated at a ventricular site during the blanking period can be detected by the IMD.

4 Claims, 7 Drawing Sheets

CARDIAC STIMULATING DEVICE

TECHNICAL FIELD

The present invention generally relates to implantable cardiac stimulating devices, and in particular to such devices capable of detecting premature ventricular contractions.

BACKGROUND

It is well-known in the art that cardiac stimulating devices can emit back-up pulses to a heart ventricle when no evoked response to a previously applied ventricular pacing pulse is detected, see U.S. Pat. No. 5,476,487.

This type of cardiac stimulating devices is generally denoted as autocapture pacemakers in the art. The autocapture pacemakers operate by sensing whether a response occurs in the ventricle shortly after a ventricular stimulating pulse has been delivered, such as 5-20 ms after delivery. The sensing may, for instance, take place during 40-80 ms. If a response is sensed during this time interval then no back-up pulse is emitted. However, if no evoked response is sensed, the pacemaker emits a back-up pulse. The back-up pulse is usually emitted with increased output energy or power in order to secure capture of the heart. For example, a normal value for a ventricular pacing pulse could have an amplitude of about 1.5V, whereas the back-up pulse can be emitted with an amplitude of about 4.5 V.

Sometimes a back-up pulse can be delivered to the ventricle during a phase of the heart cycle when a stimulating pulse is not wanted. Such unwanted pulses may be initiated, for instance, after the occurrence of a premature ventricular contraction (PVC). If such a PVC occurs more or less simultaneously with an atrial stimulating pulse, the PVC may be undersensed due to ventricular blanking after atrial stimulation. In such a case, a ventricular stimulating pulse may be delivered in the PVC refractory period, during which the heart will not respond to ventricular stimulation. No evoked response will consequently be detected and a back-up pulse is delivered. In an unfortunate case, the back-up pulse can be timed with the vulnerable phase of the PVC, typically coincident with a part of the T-wave, during which a delivered stimulating pulse may induce repetitive rhythms, such as for example tachycardia or ventricular fibrillation (VF). A back-up pulse poses somewhat higher threat due to its increased energy content.

A related problem also exists for cardiac stimulating devices not running in the autocapture operation mode. With these cardiac stimulating devices, the delivery of the ventricular stimulating pulse can coincide with the vulnerable phase of a PVC, in particular if a long atrioventricular interval has been programmed for the cardiac stimulating device. Such comparatively long atrioventricular intervals are commonly used within the field in order to avoid unnecessary ventricular stimulation.

U.S. Pat. No. 6,952,609 discloses an implantable cardiac stimulating device capable of combating problems of increased risk of unintentionally triggering tachycardia or VF due to unfortunate timing of back-up pulses. The implantable cardiac stimulating device has a control unit for controlling an atrial pulse generator dependent on an atrial sensing unit, in a first manner wherein no stimulating pulse is delivered to the atrium and in a second manner wherein stimulating pulses are delivered to the atrium. The control unit additionally prevents delivery of back-up pulses to the ventricle during a number of heart cycles when the control unit changes from the first manner of operation to the second manner of operation.

US 2004/0158292 discloses an implantable cardiac stimulating device having an atrial pulse generator capable of generating and delivering an atrial stimulating pulse to an atrium of a heart. The delivered atrial pulse triggers a blanking period, during which a PVC may occur. Atrial and ventricular sense amplifiers connected to the pace/sense electrodes of an atrial lead and a ventricular lead, respectively, are inactive during the blanking period and will not sense the PVC. It is therefore a risk that a subsequently ventricular stimulating pulse will be delivered by the implantable cardiac stimulating device during the vulnerable period of the ventricles caused by the PVC.

The implantable cardiac stimulating device consequently has a dedicated PVC sense amplifier connected to a lead electrode and a can electrode or different can electrodes to perform far field PVC sensing. The PVC sense amplifier is blanked during delivery of the atrial pulse but is then directly activated in order to be able to detect any PVC occurring in the normal blanking period of the ventricular sense amplifier.

SUMMARY

There is still a need for improvements relating to reducing the risk of unintentional triggering of tachycardia or VF due to delivery of ventricular stimulating pulses and back-up pulses in a vulnerable period.

It is an objective to provide an implantable cardiac stimulating device with reduced risk of triggering tachycardia and ventricular fibrillation.

It is a particular objective to provide an implantable cardiac stimulating device suitable for detecting PVCs.

These and other objectives are met by embodiments as defined by the accompanying patent claims.

Briefly, an implantable cardiac stimulating device comprises a lead connector electrically connectable to an atrial lead and a multi-electrode ventricular lead having at least three spatially separated electrodes. The device comprises an atrial pulse generator for generating atrial stimulating pulses and a ventricular pulse generator for generating ventricular stimulating pulses. An atrial sensing unit is implemented to sense any electric events in an atrium of a heart. A ventricular sensing unit is implemented and configured to individually sense any electric events in a ventricle of the heart using multiple, different electrode pairs of the multi-electrode ventricular lead.

A controller is connected to the pulse generators and the sensing units and controls the operation of the ventricular sensing unit. In particular, the controller is configured to blank the ventricular sensing unit during a blanking period following delivery of an atrial stimulating pulse by the atrial pulse generator. The controller then activates the ventricular sensing unit at the expiry of the blanking period to start the individual sensing at the multiple ventricular sites. The ventricular sensing unit is thereby enabled to detect a PVC depolarization wave traveling over the ventricle using at least one of the multiple, different electrode pairs even if the PVC depolarization wave was initiated at a ventricular site during the blanking period.

Thus, the reduced propagation speed over the ventricle by PVC depolarization waves is utilized with the multi-electrode ventricular lead having multiple local sensing sites distributed over the ventricle. This means that even though the PVC depolarization wave is initiated at a ventricular site during the blanking period when ventricular sensing is blanked, the reduced propagation speed implies that it is a high likelihood that the PVC depolarization wave has not yet reached and past the sensing sites of all the multiple, different electrode pairs at the end of the blanking period. The device will therefore be able to detect the PVC and prevent the delivery of a ventricular stimulating pulse or back-up pulse during the vulnerable period following the PVC.

Another aspect relates to a cardiac stimulating method comprising delivering an atrial stimulating pulse to an atrium and starting a blanking period and an atrioventricular interval based on the delivery of the atrial stimulating pulse. Individual sensing is initiated at the expiry of the blanking period and can continue up to the end of the atrioventricular interval. The individual sensing involves individually sensing for electric events at multiple sensing sites of a ventricle. These multiple sensing sites are spatially distributed over the ventricle to perform parallel sensing at different ventricular sites. If an electric event is sensed at any of the multiple sensing sites prior expiry of the atrioventricular interval no ventricular stimulating pulse is delivered to the ventricle. Correspondingly, if no electric events are sensed, a ventricular stimulating pulse is delivered at the expiry of the atrioventricular interval.

BRIEF DESCRIPTION OF THE DRAWINGS

The invention, together with further objects and advantages thereof, may best be understood by making reference to the following description taken together with the accompanying drawings, in which.

DETAILED DESCRIPTION

Figure 3:
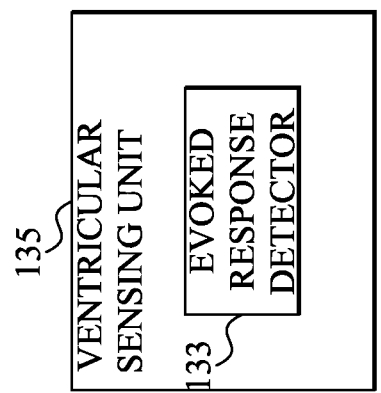
FIG. 3 is a block diagram of an embodiment of the ventricular sensing unit in the implantable cardiac stimulating device of FIG. 2.

Throughout the drawings, the same reference numbers are used for similar or corresponding elements.

The present invention generally relates to implantable medical devices (IMDs) and methods of operating such devices, and in particular to dual chamber implantable cardiac stimulating devices with increased PVC detecting capabilities.

The IMD of the invention is connectable during operation in an animal body, preferably mammalian body and more preferably a human body, with at least one so-called multi-electrode lead that is implanted in or in connection with a heart chamber, preferably the right ventricle or the left ventricle. This multi-electrode lead comprises at least three sensing electrodes provided at different spatial positions along the distal lead portion. These electrodes will therefore be distributed at different sites of the ventricle and preferably extend from or close to the apical portion of the ventricle towards the basal portion.

The inclusion of more than two electrodes in the multi-electrode lead implies that the lead comprises multiple, i.e. at least two, pairs of electrodes that can be used to sense local electric signals at different sites of the ventricle. This ability of the IMD to individually sense electric activities of the ventricle at different sites is utilized as disclosed herein to enable detection of PVCs that arise during the blanking period following a previously delivered atrial stimulating pulse.

A PVC originates from a single focus in the ventricle. The propagation of the PVC depolarization wave over the ventricles takes much longer time as compared to a depolarization wave made through the heart conduction system. There is actually a significant difference in times between achieving depolarization of the entire ventricles via a depolarization wave originating from a single PVC focus outside the heart conduction system as compared to the normal depolarization wave propagation over the ventricles by means of the electrical conduction system of the heart, e.g. a depolarization wave initiated by the heart's sinus node. As is well known in the art, the depolarization propagation for an intrinsic electric event in the ventricles originates from the atrioventricular (AV) node in the wall separating the atria and the ventricles. The depolarization continues past the AV node via the bundle of His where it is divided and conducted down to the apex via the right and left bundle branches to spread over the myocardium through the Purkinje fibers. This conduction system is designed to rapidly conduct the depolarization and spread it over the ventricles. As a consequence, the depolarization wave quickly propagates over the ventricles.

The reduced propagation speed of a PVC depolarization wave as compared to the normal depolarization wave is employed by the invention. Thus, by having multiple spatially separated local detection sites throughout the ventricle, the IMD connectable to the multi-electrode lead has significantly increased chances of detecting the propagating PVC depolarization wave after expiry of the blanking period.

Figure 4:
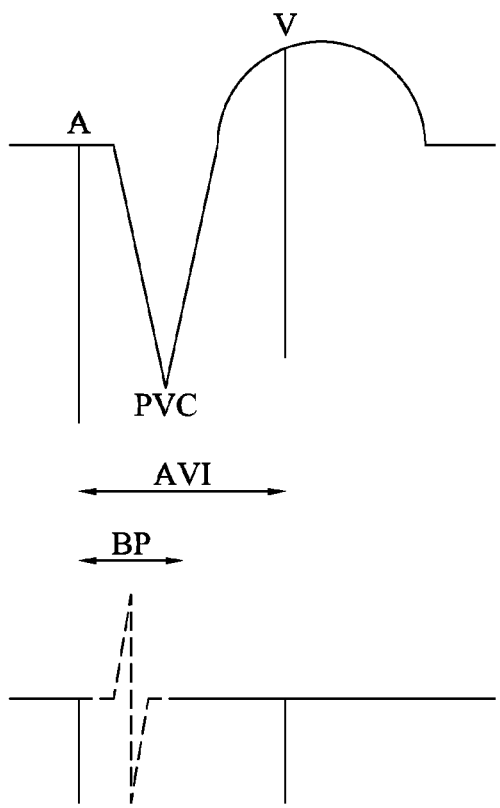
FIG. 4 illustrates problems with prior art implantable cardiac stimulating devices for which a premature ventricular contraction occurs during the blanking period.
Figure 4:
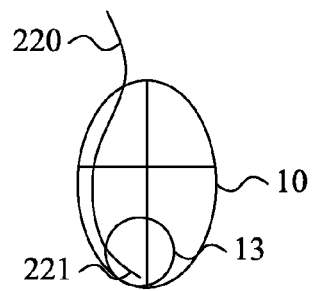
Figure 5:
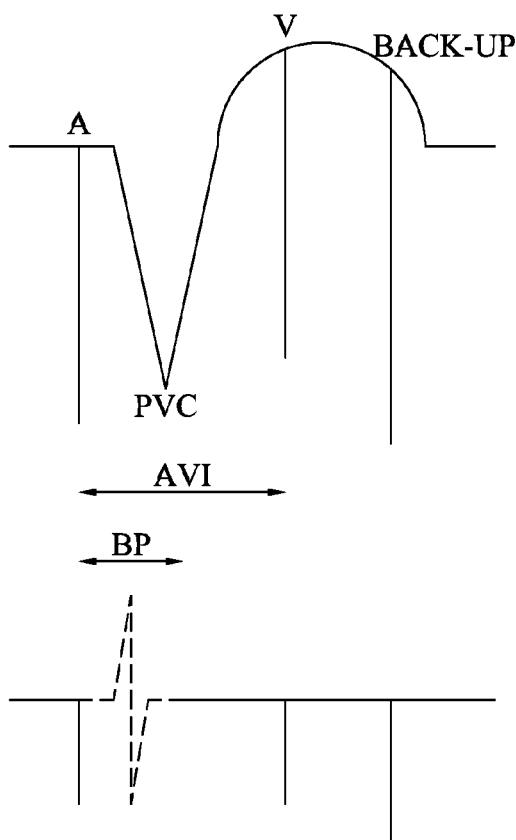
FIG. 5 illustrates problems with prior art implantable cardiac stimulating devices for which a back-up pulse is delivered during the vulnerable period of a premature ventricular contraction.
Figure 5:
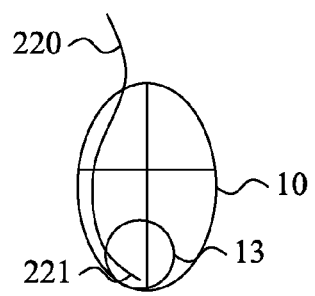
Figure 6:
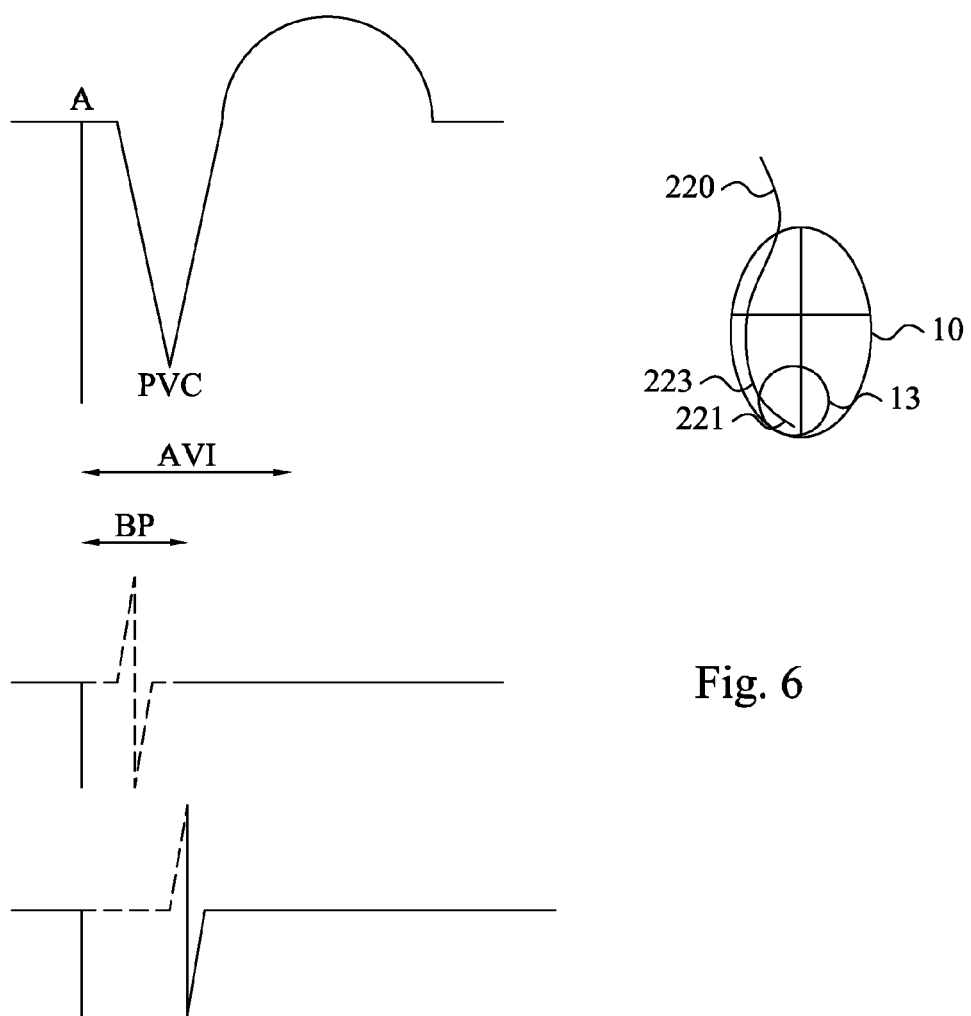
FIG. 6 illustrates detection of a premature ventricular contraction with an implantable cardiac stimulating device according to an embodiment.

Advantages of the embodiments in the light of the prior art will be further described herein in connection with FIGS. 4-6 to illuminate technical features of the embodiments. FIG. 4 schematically illustrates on the right hand side a heart 10 with a prior art bipolar cardiac lead 220 introduced in the right ventricle. The lead 220 only comprises, in this prior art example, two electrodes, generally a tip electrode and a ring electrode. As a consequence, only a single electrode pair 221 capable of sensing electric events of the right ventricle is available.

The left hand side of the figure illustrates a surface electrocardiogram (ECG) in the top and an intracardiac electrogram (IEGM) in the bottom from the electrode pair 221. In this illustrative example, the IMD has generated and via the cardiac lead 220 delivered an atrial stimulating pulse (A) to a heart atrium by an atrial lead not illustrated in the figure. The delivery of the atrial stimulating pulse triggers a blanking period (BP). During this blanking period the ventricular sensing unit of the IMD is temporarily disconnected from the electrode pair 221 implying that electric events occurring in the ventricles of the heart 10 during this blanking period will not be detected by the IMD. This is schematically illustrated in the figure by hatching the part of the IEGM corresponding to the blanking period.

Delivery of the atrial stimulating pulse also triggers an atrioventricular interval (AVI) during which the IMD senses for any following electric event in the ventricle, i.e. an intrinsic ventricular pulse. Though, the AVI is generally started at the delivery of the atrial stimulating pulse, the first part of the AVI, which corresponds to the blanking period, cannot be used for sensing.

If a PVC occurs shortly following the delivery of the atrial stimulating pulse, i.e. during the blanking period, it will not be sensed by the electrode pair 221 and therefore not detected by the IMD. Once the blanking period has ended, the PVC depolarization wave 13 has, in this example, already propagated past the electrode pair 221, which is schematically illustrated in the figure. This means that after the end of the blanking period, the PVC depolarization wave 13 has been propagated from the PVC focus past the electrode pair and is now too remote from the electrode pair 221 to be accurately detected.

Since the PVC is not detected in this prior art example, a ventricular stimulating pulse (V) will be delivered to the ventricle of the heart 10 using the cardiac lead 220 at the end of the AVI. This ventricular stimulating pulse may occur in connection with the vulnerable period following the PVC, typically coincident with a part of the T-wave. Delivery of a ventricular stimulating pulse during this vulnerable period may induce repetitive rhythms, such as for example tachycardia or ventricular fibrillation.

The above-mentioned problem can occur with IMDs operating in the autocapture mode but also for IMDs that are not configured to perform autocapture operation.

FIG. 5 illustrates another problem of the prior art with IMDs operating in the autocapture mode. In this case the PVC occurs during the blanking period following a previously delivered atrial stimulating pulse as in FIG. 4. The PVC depolarization wave is not detected by the single electrode pair 221 of the cardiac lead 220 and consequently a ventricular stimulating pulse is generated and delivered after the end of the AVI. The delivery of the ventricular stimulating pulse may be coordinated to occur in the refractory period after the PVC and will consequently not trigger depolarization of the ventricle. The IMD consequently generates and delivers a back-up pulse that is delivered to the heart. This back-up pulse may fall within the vulnerable period after the PVC, with the enhanced risk of inducing tachycardia or ventricular fibrillation, a threat that is further enhanced by the higher energy in the back-up pulse.

In clear contrast to the prior solutions as illustrated in FIGS. 4 and 5, the embodiments relates to an IMD connectable to a multi-electrode lead 220 as illustrated in FIG. 6. The multi-electrode lead 220 comprises at least two electrode pairs 221, 223 spatially provided at different sites of the ventricle. Similarly to the prior art, the electrical sensing in the ventricle is temporarily blanked during the blanking period, implying that the PVC depolarization occurring close to one of the electrode pairs 221 will not be detected during the blanking period. However, as the PVC depolarization wave 13 propagates from the single start site and due to the reduced speed of PVC depolarization waves 13 it will, in this example, reach the site of the second electrode pair 223 after expiry of the blanking period. Consequently, the IMD will sense and detect the PVC during the AVI following delivery of the atrial stimulating pulse. This means that no ventricular stimulating pulse is generated for the current cardiac cycle. There is therefore no risk of triggering tachycardia or ventricular fibrillation by stimulating or applying back-up pulses in the vulnerable period or stimulating in the refractory period of the PVC as in FIGS. 4 and 5.

Figure 1:
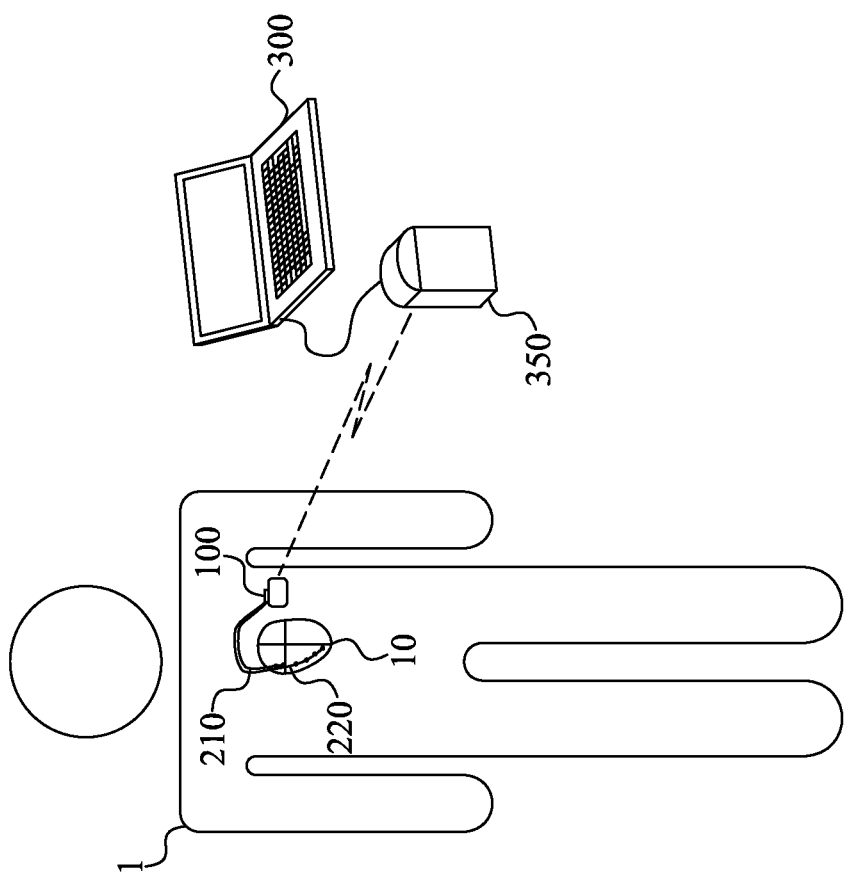
FIG. 1 is a schematic overview of a subject equipped with an implantable cardiac stimulating device according to an embodiment.

FIG. 1 is a schematic overview of a human patient 1 having an IMD 100. In the figure, the IMD 100 is illustrated as a device that monitors and/or provides therapy to the heart 10 of the patient 1, such as a pacemaker, cardiac defibrillator or cardioverter capable of delivering stimulating cardiac pacing therapy. The IMD 100 is, in operation, connected to two or more, two in the figure, cardiac leads 210, 220 inserted into or provided in connection with heart chambers, preferably in the form of at least one atrial lead 210 and at least one ventricular lead 220, which is a so-called multi-electrode lead 220.

The figure also illustrates an external programmer or clinician's workstation 300 that can communicate with the IMD 100, optionally through a communication unit 350 that operates similar to a base station on behalf of the programmer 300. As is well known in the art, such a programmer 300 can be employed for transmitting IMD programming commands, causing a reprogramming of different operation parameters and modes of the IMD 100. Furthermore, the IMD 100 can upload diagnostic data descriptive of different medical parameters or device operation parameters collected by the IMD 100 to the programmer 300.

Figure 2:
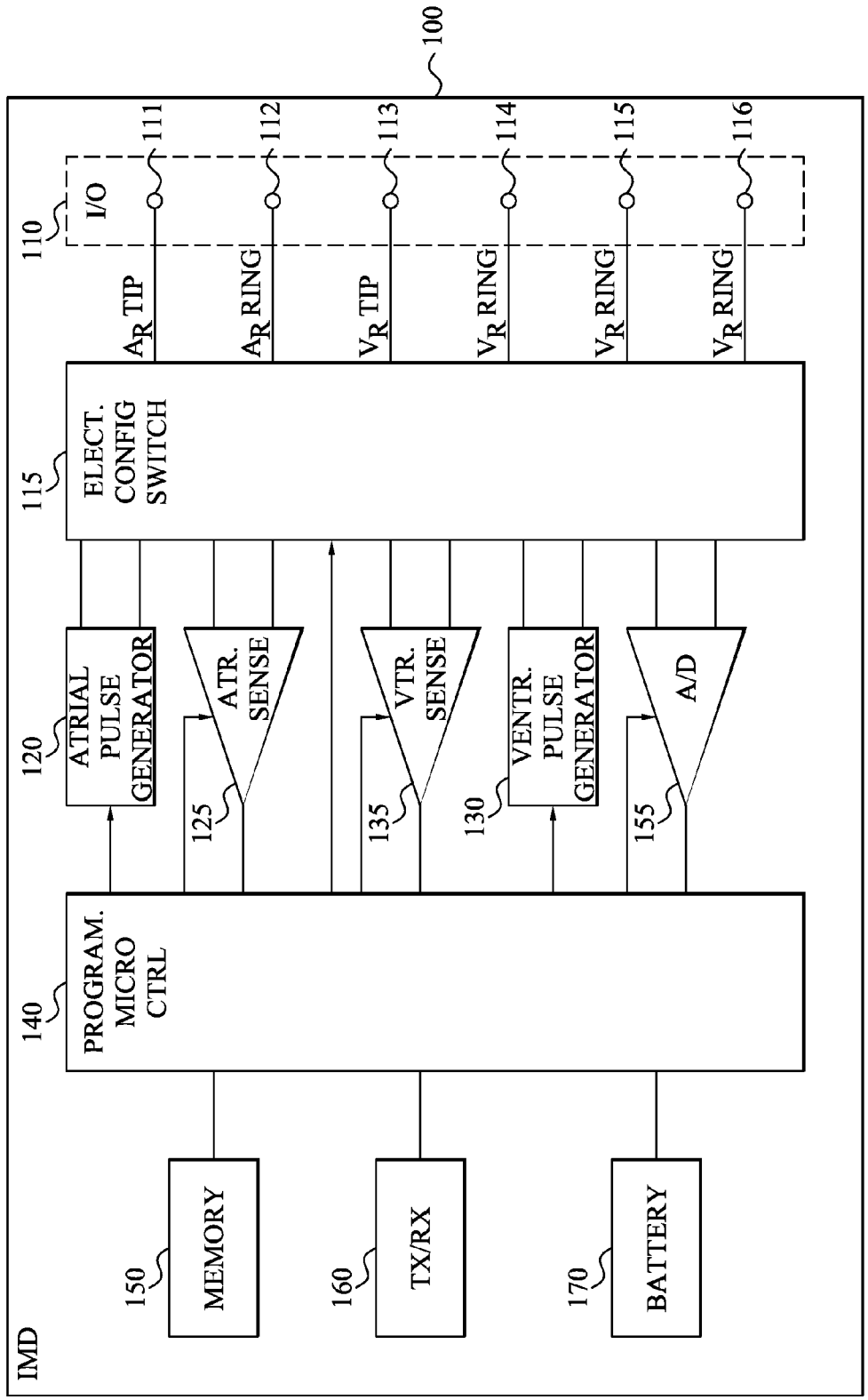
FIG. 2 is block diagram of an embodiment of an implantable cardiac stimulating device.

FIG. 2 illustrates an embodiment of an IMD 100 suitable for delivering cardiac therapy to a heart of a subject. The figure is a simplified block diagram depicting various components of the IMD 100. While a particular multi-chamber device is shown in the figure, it is to be appreciated and understood that this is done merely for illustrative purposes. Thus, the techniques and methods described below can be implemented in connection with other suitably configured IMDs as long as the IMD is capable of dual chamber operation with both atrial and ventricular sensing and stimulation. Accordingly, the person skilled in the art can readily duplicate, eliminate, or disable the appropriate circuitry in any desired combination to provide an IMD capable of treating the appropriate heart chamber(s) with pacing stimulation and optionally also cardioversion and/or defibrillation.

The IMD 100 comprises a housing, often denoted as can or case in the art. The housing can act as return electrode for unipolar leads, which is well known in the art. The IMD 100 also comprises a lead connector or input/output (I/O) 110 having, in this embodiment, a plurality of terminals 111-116. With reference to FIGS. 2 and 7-9, the lead connector 110 is configured to be, during operation in the subject body, electrically connectable to at least one atrial lead 210 and at least one multi-electrode ventricular lead 220, 230. The lead connector 110 consequently comprises terminals 111, 112 that are electrically connected to matching electrode terminals of an atrial lead 210 when the atrial lead 210 is introduced in the lead connector 110. For instance, one of these terminals 111 can be designed to be connected to a right atrial tip terminal of the atrial lead 210, which in turn is electrically connected through a conductor running along the lead body to a tip electrode 212 present at the distal end of the atrial lead 210 in the right atrium 18 of the heart 10. A corresponding terminal 112 is then connected to a right atrial ring terminal of the atrial lead 210 that is electrically connected by another conductor in the lead body to a ring electrode 214 present in connection with the distal part of the atrial lead 210, though generally distanced somewhat towards the proximal lead end as compared to the tip electrode 212.

In an alternative implementation, the IMD 100 is not connectable to a right atrial lead 210 but instead to a left atrial lead configured for implantation in the left atrium 16. A further possibility is to have an IMD 100 with a lead connector 110 having sufficient terminals to allow the IMD 100 to be electrically connectable to both a right atrial lead 210 and a left atrial lead.

Figure 7:
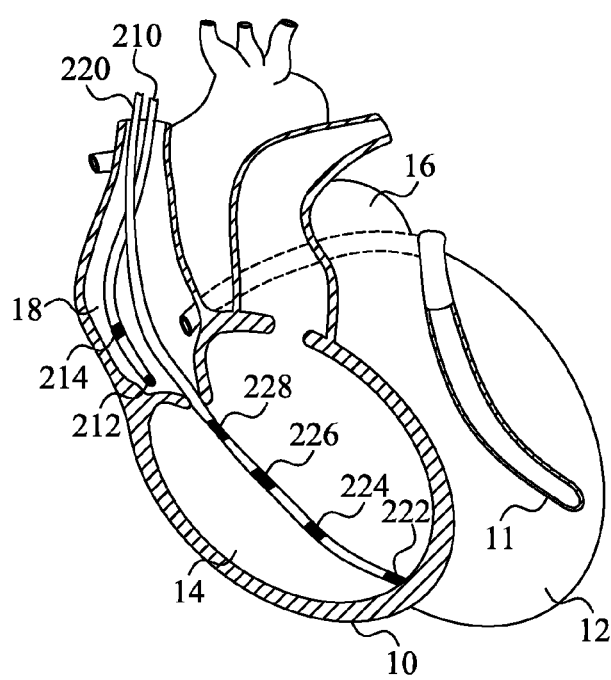
FIG. 7 illustrates a set of cardiac leads connectable to an implantable cardiac stimulating device according to an embodiment.

In order to support right chamber sensing and pacing, the lead connector 110 further comprises a right ventricular tip terminal 113 and multiple right ventricular ring terminals 114-116, which are adapted for connection to a right ventricular tip electrode 222 and respective right ventricular ring electrodes 224-228 of a multi-electrode right ventricular lead 220 implantable in the right ventricle 14, see FIG. 7.

Figure 8:
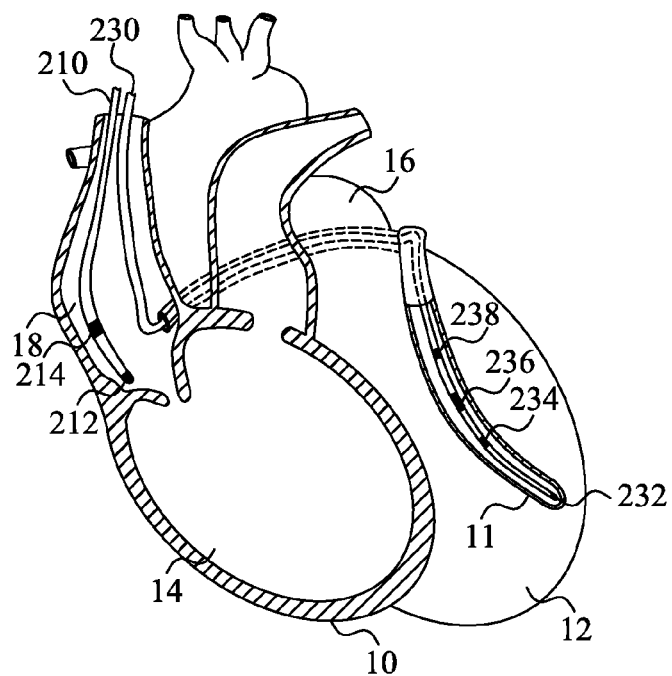
FIG. 8 illustrates another set of cardiac leads connectable to an implantable cardiac stimulating device according to an embodiment.

In an alternative embodiment, the lead connector 110 is connectable to a multi-electrode left ventricular lead 230 instead of a multi-electrode right ventricular lead 220, see FIG. 8. A multi-electrode left ventricular lead 230 is typically implanted in the coronary venous system 11 for safety reasons although implantation inside the left ventricle 12 has been proposed in the art. In the following, "left ventricular lead" 230 is used to describe a cardiac lead designed to provide sensing and pacing functions to the left ventricle 12 regardless of its particular implantation site, i.e. inside the left ventricle 12 or in the coronary venous system 11. The left ventricular lead 230 preferably also comprises a tip electrode 232 and multiple ring electrode 234-238.

Figure 9:
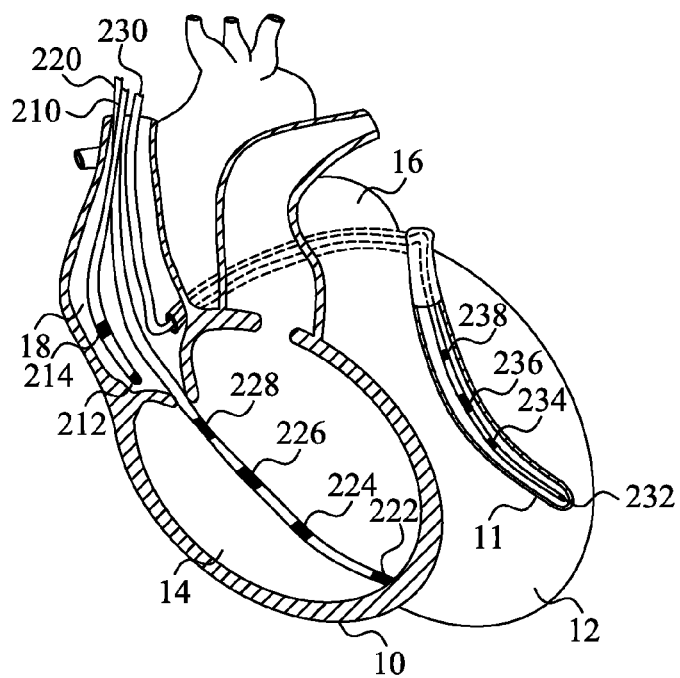
FIG. 9 illustrates a further set of cardiac leads connectable to an implantable cardiac stimulating device according to an embodiment.

Also a combination of a multi-electrode right ventricular lead 220 and a multi-electrode left ventricular lead 230 can be used with the IMD 100 with a lead connector 110 then having the appropriate number of terminals, see FIG. 9. In such a case, sensing and detection of PVCs as disclosed herein can be conducted in both ventricles 12, 14. The continuing description of embodiments therefore applies to sensing in the right ventricle, sensing in the left ventricle or sensing both in the right and left ventricles, depending on the particular multi-electrode ventricular lead(s) 220, 230 that is(are) connectable to the IMD 100.

As an alternative to the embodiment illustrated in FIG. 9, one of the ventricular leads 220, 230 does not have to be a multi-electrode lead 220, 230 but can instead be a unipolar lead only having a tip electrode or a bipolar lead having a tip electrode and a single ring electrode.

In the FIGS. 7-9, the multi-electrode ventricular leads 220, 230 have been exemplified by quadropolar leads 220, 230 each having four electrodes 222-228, 232-228, preferably one tip electrode 222, 232 and three respective ring electrodes 224-228, 232-238. An alternative design of a quadropolar lead instead has four ring electrodes and no tip electrode.

The multi-electrode ventricular lead connectable to the IMD 100 must not necessarily be a quadropolar lead. In clear contrast, the important feature is that is comprises at least three spatially separated electrodes along the distal portion of the lead to thereby achieve at least two different electrode pairs that can be used for sensing electric events at different sites of the ventricle. Therefore, alternative implementations of a multi-electrode ventricular lead can have three, four, five, six, seven, eight, nine, ten or even more spatially separated electrodes present inside or in connection with a ventricle 12, 14 of the heart.

The IMD 100 as illustrated in FIG. 2 comprises an atrial pulse generator 120 and a ventricular pulse generator 130 that generate pacing pulses for delivery by the atrial lead(s) and the ventricular lead(s) preferably through an electrode configuration switch 115.

It is understood that in order to provide stimulation therapy in different heart chambers, the atrial and ventricular pulse generators 120, 130 may include dedicated, independent pulse generators, multiplexed pulse generators, or shared pulse generators. The pulse generators 120, 130 are controlled by a controller 140 via appropriate control signals, respectively, to trigger or inhibit the stimulating pulses.

The IMD 100 also comprises a controller 140, preferably in the form of a programmable microcontroller 140 that controls the operation of the IMD 100. The controller 140 typically includes a microprocessor, or equivalent control circuitry, designed specifically for controlling the delivery of pacing therapy, and may further include RAM or ROM memory, logic and timing circuitry, state machine circuitry, and I/O circuitry. Typically, the controller 140 is configured to process or monitor input signal as controlled by a program code stored in a designated memory block. The type of controller 140 is not critical to the described implementations. In clear contrast, any suitable controller may be used that carries out the functions described herein. The use of microprocessor-based control circuits for performing timing and data analysis functions are well known in the art.

The controller 140 further controls the timing of the stimulating pulses, such as pacing rate, AVI, atrial escape interval (AEI) etc. as well as to keep track of the timing of refractory periods, blanking periods, noise detection windows, evoked response windows, alert intervals, marker channel timing, etc.

A preferred electronic configuration switch 115 includes a plurality of switches for connecting the desired terminals 111-116 to the appropriate I/O circuits, thereby providing complete electrode programmability. Accordingly, the electronic configuration switch 115, in response to a control signal from the controller 140, determines the polarity of the stimulating pulses (e.g., unipolar, bipolar, combipolar, etc.) by selectively closing the appropriate combination of switches (not shown) as is known in the art.

An atrial sensing circuit or detector 125 and a ventricular sensing circuit or detector 135 are also selectively coupled to the atrial lead(s) and the ventricular lead(s) through the switch 115 for detecting the presence of cardiac activity in the heart chambers. Accordingly, the atrial and ventricular sensing circuits 125, 135 may include dedicated sense amplifiers, multiplexed amplifiers, or shared amplifiers. The switch 115 determines the "sensing polarity" of the cardiac signal by selectively closing the appropriate switches, as is also known in the art. In this way, the clinician may program the sensing polarity independent of the stimulation polarity. The sensing circuits are optionally capable of obtaining information indicative of tissue capture as is further mentioned herein.

Each sensing circuit 125, 135 preferably employs one or more low power, precision amplifiers with programmable gain and/or automatic gain control, band-pass filtering, and a threshold detection circuit, as known in the art, to selectively sense the cardiac signal of interest.

The outputs of the atrial and ventricular sensing circuits 125, 135 are connected to the controller 140, which, in turn, is able to trigger or inhibit the atrial and ventricular pulse generators 120, 130, respectively, in a demand fashion in response to the absence or presence of cardiac activity in the appropriate chambers of the heart.

Furthermore, the controller 140 is also capable of analyzing information output from the sensing circuits 125, 135 and/or a data acquisition system 155 to determine or detect whether and to what degree tissue capture has occurred and to program a pulse, or pulse sequence, in response to such determinations. The sensing circuits 125, 135, in turn, receive control signals over signal lines from the controller 140 for purposes of controlling the gain, threshold, polarization charge removal circuitry, and the timing of any blocking circuitry coupled to the inputs of the sensing circuits 125, 135 as is known in the art.

Cardiac signals are also applied to inputs of an optional analog-to-digital (A/D) data acquisition system 155. The data acquisition system 155 is configured to acquire intracardiac electrogram signals, convert the raw analog data into a digital signal, and store the digital signals for later processing and/or transmission to the programmer by a transceiver 160. The data acquisition system 155 is coupled to the atrial lead and/or the ventricular lead through the switch 115 to sample cardiac signals across any pair of desired electrodes.

The controller 140 is further coupled to a memory 150 by a suitable data/address bus, wherein the programmable operating parameters used by the controller 140 are stored and modified, as required, in order to customize the operation of the IMD 100 to suit the needs of a particular patient. Such operating parameters define, for example, pacing pulse amplitude, pulse duration, electrode polarity, rate, sensitivity, automatic features, and time interval between pacing pulse of an applied pacing pulse sequence.

Advantageously, the operating parameters of the IMD 100 may be non-invasively programmed into the memory 150 through a transceiver 160 in communication via a communication link with the previously described communication unit of the programmer. The controller 140 activates the transceiver 160 with a control signal. The transceiver 160 can alternatively be implemented as a dedicated receiver and a dedicated transmitter connected to separate antennas or a common antenna, preferably a radio frequency (RF) antenna.

The IMD 100 additionally includes a battery 170 that provides operating power to all of the circuits shown in FIG. 2.

The ventricular sensing unit 135 preferably comprises an evoked response detector 133, which is illustrated in the schematic block diagram of FIG. 3. The evoked response detector 133 is in particular implemented in the IMD for detecting an evoked response of a heart ventricle in response to a ventricular stimulating pulse previously generated by the ventricular pulse generator 130 and delivered to the ventricle by the connected ventricular lead. In an embodiment, the evoked response detector 133 generates an evoked response detection signal upon detection of an evoked response of the monitored ventricle(s). This detection signal is forwarded to the controller 140 and is employed for the IMD control. In FIG. 3, the evoked response detector 133 has been illustrated as forming part of the ventricular sensing unit 135. An alternative embodiment has the evoked response detector 133 implemented elsewhere in the IMD preferably connected to the controller and the switch. In a further alternative embodiment, the evoked response detecting function of the evoked response detector 133 is performed by the ventricular sensing unit 135, which then has dual functions. The evoked response detector 133 is only required if the IMD is running according to the autocapture mode and can therefore be absent in IMDs not configured according to autocapture operation.

The ventricular sensing unit 135 is configured to individually sense electric events in the heart ventricle using multiple, different pairs of electrodes of the multi-electrode ventricular lead(s). This means that sensing can take place individually at multiple ventricular sites using the different electrode pairs. The ventricular sensing unit 135 is preferably configured, with the switch 115, to simultaneously sense using the multiple electrode pairs. This means that if the electrodes of the multi-electrode lead can be divided into three electrode pairs, sensing is preferably possible simultaneously on three channels and at three different ventricular sites.

The electrodes of the multiple electrode pairs are preferably spatially neighboring or adjacent electrodes as arranged along the length of the multi-electrode ventricular lead. For instance, if the multi-electrode ventricular lead is a quadropolar lead comprising a tip electrode and three ring electrodes, three different pairs of spatially neighboring electrodes are possible. The first electrode pair involves the tip electrode and the most distal ring electrode. The second electrode pair comprises the most distal ring electrode and the middle ring electrode with the third and final electrode pair comprising the middle and the most proximal ring electrodes. Generally, a multi-electrode having N electrodes enables individual sensing using N−1 different electrode pairs with spatially neighboring electrodes.

The usage of spatially neighboring electrodes is preferred to thereby enable local detection of the electric events occurring at the part of the ventricle that is present between the neighboring electrodes. This means that individual and local sensing is possible by the IMD 100 of FIG. 2 with such a multi-electrode ventricular lead.

The controller 140 of the IMD 100 is configured to blank the ventricular sensing unit 135 and preferably the atrial sensing unit 125 during a blanking period following delivery of an atrial stimulating pulse from the atrial pulse generator 120. Blanking generally involves uncoupling the ventricular sense amplifier(s) and the atrial sense amplifier(s) from the respective atrial and ventricular sense electrode pairs following delivery of the atrial stimulating pulse. Blanking can be affected by the controller 140 signaling the switch 115 to temporarily disconnect the ventricular sensing unit 135 and preferably the atrial sensing unit 125 from the terminals 111-116 during this blanking period.

The controller 140 is further configured to activate the ventricular sensing unit 135 at the expiry of the blanking period, such as by controlling the switch 115 to establish electric contact between the ventricular sensing unit 135 and the terminals 113-116 connectable to the multi-electrode ventricular lead. The activation of the ventricular sensing unit 135 at the expiry of the blanking period enables the ventricular sensing unit to detect any PVC depolarization wave traveling over the ventricle using at least one of the multiple electrode pairs of the multi-electrode ventricular lead.

The controller 140 preferably starts the previously mentioned AVI when the atrial pulse generator 120 generated an atrial stimulating pulse that is delivered to the atrium through the switch 115, terminals 111, 112 and the atrial lead. The ventricular sensing of the ventricular sensing unit 135 is then conducted up to the end of the AVI, i.e. from the expiry of the blanking period and up to the end of the AVI. If the ventricular sensing unit 135 detects an electric event, such as a propagating PVC depolarization wave with any of the electrode pairs, a sense signal is forwarded to the controller 140. The controller 140 thereby controls the ventricular pulse generator 130 to prevent the ventricular pulse generator 130 from generating a ventricular simulating pulse at the expiry of the AVI. Thus, if a PVC is detected by the IMD 100 no ventricular stimulating pulse will be delivered during the cardiac cycle. However, if no electric events have been detected with any of the multiple electrode pairs in or in connection with the ventricle at the expiry of the AVI, the controller 140 controls the ventricular pulse generator 130 to generate a ventricular stimulating pulse that is delivered through the switch 115 and one terminal (unipolar) or two terminals (bipolar) connected to the multi-electrode ventricular lead.

If the IMD 100 is running according to the autocapture mode, the controller starts an evoked response time window at the delivery of the ventricular stimulating pulse. The optional evoked response detector 133 then monitors for any capture and evoked response during the evoked response window. If evoked response is not detected, the controller 140 controls the ventricular pulse generator 130 to generate and deliver a back-up pulse at the end of the evoked response window.

Figure 10:
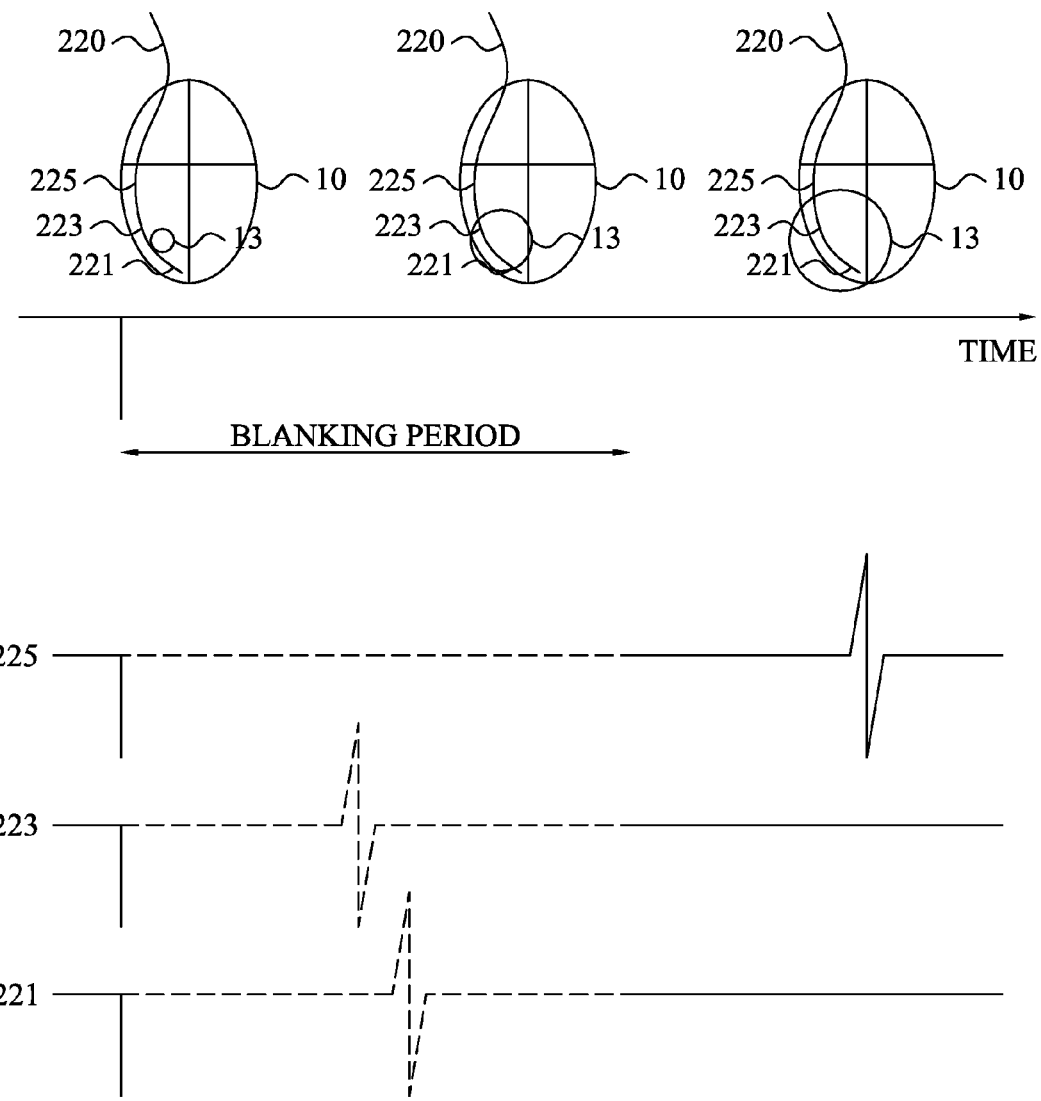
FIG. 10 is a timing/waveform diagram illustrating propagation and detection of a premature ventricular contraction depolarization wave.

FIG. 10 illustrates the concept of sensing for electric activity at multiple different sites of a ventricle using a quadropolar ventricular lead 220. The figure illustrates at the top three different time instances and the propagation of a PVC depolarization wave 13 relative three electrode pairs 221, 223, 225 employed for sensing. As is indicated in the figure, once the PVC depolarization wave 13 is propagating past the two most distal electrode pairs 221, 223, the ventricular sensing unit connected to the electrodes of the quadropolar ventricular lead 220 is still blanked since the blanking period is running. The PVC depolarization wave 13 is therefore not detected by these electrode pairs 221, 223, which has been indicated by hatching. However, after the expiry of the blanking period and the onset of ventricular sensing, the PVC depolarization wave 13 has not yet propagated past the site of the most proximal electrode pair 225. This means that the PVC depolarization wave 13 will be sensed by the IMD with this electrode pair 225 once the PVC depolarization wave 13 reaches the ventricular site sensed by the electrode pair 225.

US 2004/0158292 mentioned above discloses a technique based on far field sensing using a dedicated far field PVC sense amplifier that is active during the blanking period. That technique is fundamentally different from the solution proposed by the embodiments and disclosed herein. Additionally, the prior art far field sensing is marred by several disadvantages.

The embodiments having a dedicated far field PVC sense amplifier connected between different can electrodes requires complicated IMD housings with feed throughs, implying complicated assembly and problems with electric isolation of the can electrodes from each other. Additionally, it is hard to capture far field PVC signals only with can electrodes since the distance between them is minimal. Additionally, the antenna vector formed by the can electrodes is not in optimal direction as compared to the far field PVC vector. The can electrodes will further be in close contact to the body muscles with accompanying increased risk of myopotential sensing.

The embodiments that have a dedicated PVC sense amplifier connected to an electrode on the cardiac lead and a can electrode, i.e. unipolar sensing, also have accompanying problems with sensing myopotentials and electromagnetic interference (EMI).

Far field PVCs have a significant lower amplitude and slew-rate as compared to PVCs sensed locally in the ventricle through bipolar sensing. The amplitude and slew-rate of a far field PVC additionally decreases with increased distance to the PVC and the slew-rate also decreases with increased distance between the sensing electrodes. This means that the amplifier implemented in the IMD for far field PVC sensing must have a higher sensitivity and a broader band-pass filter configured for lower signal frequencies. However, this implies that the amplifier also becomes more sensitive to undesired sensing of myopotentials and low-frequency EMI.

If oversensing by the far field PVC amplifier occurs after delivery of an atrial stimulating pulse, ventricular stimulation will for safety reasons often be programmed to be delivered with shortened AVI even if intrinsic atrial-to-ventricular conduction through the AV node is present. If undersensing by the far field PVC amplifier occurs after delivery of an atrial stimulating pulse, ventricular stimulation coinciding with the T wave of the PVC may occur if a long AVI has been programmed. This means that the specific design of the far field PVC amplifier has an increased risk of inducing tachycardia or ventricular fibrillation if undersensing occurs.

There is a significant risk with far field sensing that myopotentials, EMI or other background signals are detected by the far field PVC amplifier and interpreted as a PVC. In such a case, the AVI is reduced (if programmed ON for safety reason as previously mentioned) and there is a restart of the ventricular-to-atrial interval. This includes atrial refractory time. As a consequence, the possibility of correctly detecting atrial electric events (P wave) is reduced. A next ventricular stimulating pulse that would be desired might actually not occur or an intrinsic ventricular depolarization might be interpreted as a PVC.

Additionally, the IMD in the prior art has both a far field PVC sense amplifier and a traditional ventricular sense amplifier bipolarly connected to lead electrodes. There might be a competition between these two sense amplifiers. This is solved by activating the PVC sense amplifier only during the blanking period for the ventricular sense amplifier. However, the PVC sense amplifier still has its own blanking period, though, shorter than the one of the ventricular sense amplifier to prevent detection of the atrial stimulating pulse. This means that the sensing time period of the PVC sense amplifier will only be from the end of its blanking period to the end of the blanking period of the ventricular sense amplifier.

The above mentioned problems of the prior art techniques are solved by embodiments that utilize a local sensing and PVC detection at multiple ventricular sensing sites.

Embodiments of the IMD 100 as disclosed in FIG. 2 connectable to a multi-electrode ventricular lead can not only be employed for detecting a PVC depolarization wave that is initiated at a ventricular site during the blanking period following atrial stimulation. It is actually possible to employ the difference in propagation velocity of PVC depolarization waves and normal depolarization waves to classify a detected electric event as either being due to a PVC or intrinsic ventricular depolarization.

In this embodiment, the ventricular sensing unit 135 is capable of detecting a depolarization wave using at least two electrode pairs of the multiple, different electrode pairs of the multi-electrode ventricular lead. The controller 140 is then configured to calculate a time period from detection of the depolarization wave at a first electrode pair up to detection of the depolarization wave at a second electrode pair. The calculated time period is then employed by the controller 140 to classify the depolarization wave as originating from a PVC or an intrinsic depolarization. Thus, the time required for the depolarization wave to propagate between the two electrode pairs depends on the propagation speed since the distance between the electrode pairs is fixed. The memory 150 of the IMD 100 preferably stores respective threshold times that are employed by the controller 140 to compare with the calculated time period. Thus, if the calculated time period for a given electrode pair combination is below a defined threshold time from the memory 150, the detected depolarization wave is classified as an intrinsic depolarization wave, otherwise it is regarded as being due to a PVC.

The memory 150 preferably comprises such a threshold time for each combination of electrode pairs of the multi-electrode ventricular lead. In such a case, the controller 140 retrieves the relevant threshold time based on which electrode pairs that were able to capture the depolarization wave.

In an alternative approach, the memory 150 can comprise distance data relating to each combination of electrode pairs. Thus, the memory 150 includes information of the spatial distance between the electrode pairs in the ventricle. The distance can be an estimated distance that is equal to the actual distance between the electrode pairs along the multi-electrode ventricular lead. In a more elaborated embodiment, an x-ray image has been taken on the multi-electrode ventricular lead after implantation. The physician can then measure the actual distance between the electrode pairs after implantation and use the programmer to download this data to the memory 150 through the transceiver 160 and controller 140.

In this embodiment, the controller 140 calculates an estimated velocity of the detected depolarization wave based on the calculated time period and the distance data applicable to the given electrode pair combination and fetched from the memory 150. The controller 140 can then conclude whether the depolarization wave is due to a PVC or an intrinsic depolarization based on whether the estimated velocity is below or exceeds a threshold velocity preferably stored in the memory 150.

The detection of a PVC by the IMD 100 can be used in to trigger different IMD operation algorithms that are today initiated based on PVC detection. For instance, A pace on PVC is a non-limiting example of such an algorithm that can be initiated when the IMD 100 detects a PVC by means of the individual sensing at multiple ventricular sites by the multi-electrode ventricular lead.

Embodiments as disclosed herein are advantageous when the IMD 100 is programmed to the DDD(R), DVI(R), DDT(R) or DDI(R) pacing modes.

Figure 11:
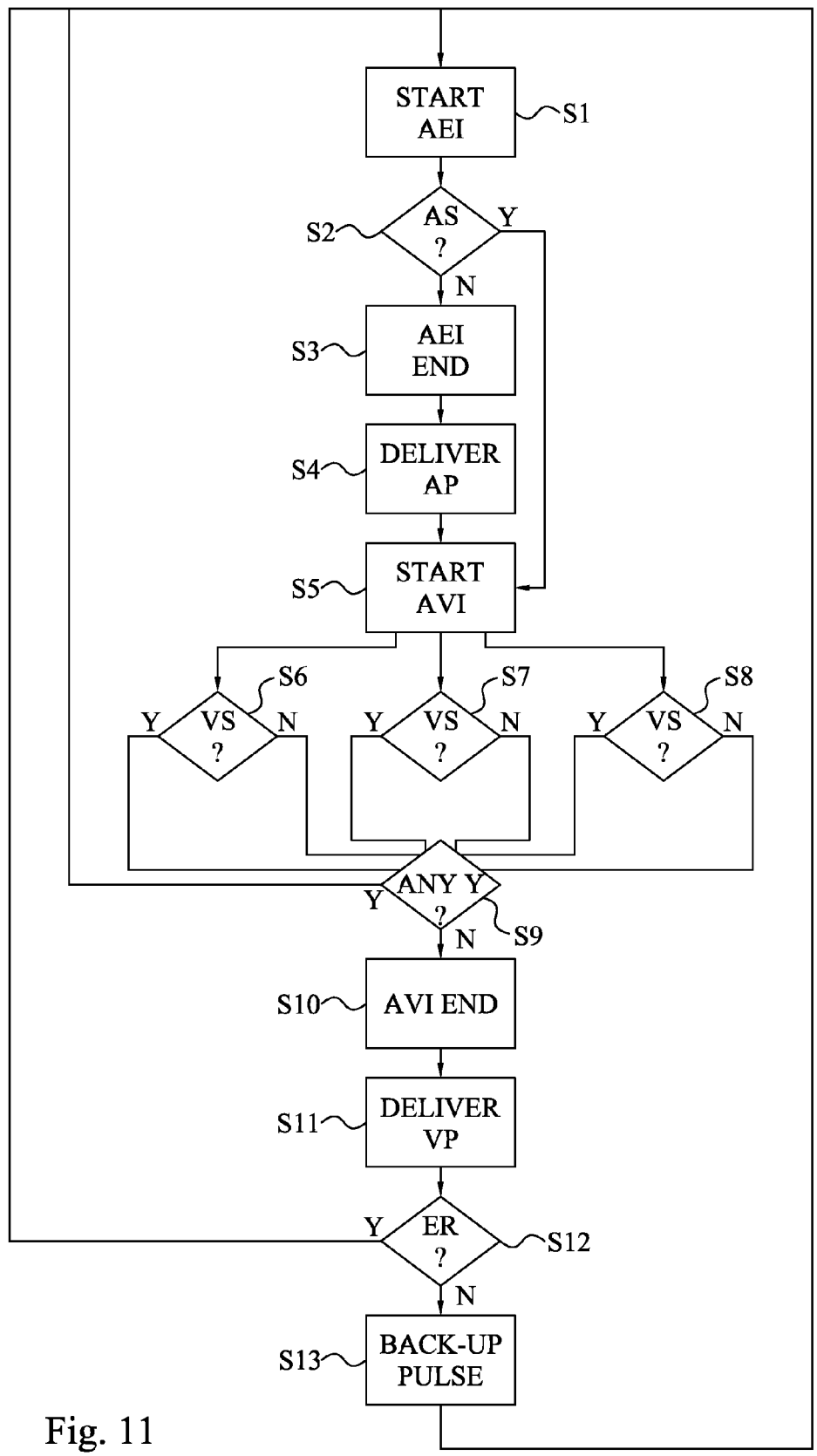
FIG. 11 is flow diagram illustrating a cardiac stimulating method.

FIG. 11 is a flow diagram illustrating a cardiac stimulating method. The method starts in step S1, where an AEI is set to indicate a new cardiac or heart cycle. The AEI indicates the atrial escape interval and is a time interval that starts with an atrial or a ventricular sensed or paced event of the preceding heart cycle. Thus in an embodiment, an AEI runs from the atrial sensing unit 125 sensing an electric event in the atrium or the atrial pulse generator 120 generating an atrial stimulating pulse. In another embodiment, the AEI runs from ventricular sensing unit 135 sensing an electric event in the ventricle or the ventricular pulse generator 130 generating a ventricular stimulating pulse. The AEI is also restarted by a PVC sensed outside the AVI.

The controller 140 controls the atrial sensing unit 125 to sense for any atrial event during the time window of the AEI in step S2. If an atrial event is sensed by the atrial sensing unit 125 the operation continues to step S5. However, if no atrial event is sensed following expiry of the AEI in step S3, the controller 140 controls the atrial pulse generator 120 to generate an atrial stimulating pulse that is delivered to the atrium in step S4. Generating an atrial stimulating pulse in step S4 or sensing an intrinsic atrial event step S2 starts an AVI in step S5.

The controller 140 controls the ventricular sensing unit 135 to individually sense for any ventricular event at the multiple sensing sites that are spatially distributed over the ventricle during the time window of the AVI but after the end of the blanking period in steps S6-S8. Steps S6-S8 schematically illustrate the parallel, individual sensing using multiple different electrode pairs of the multi-electrode ventricular lead. In a next step S9, the controller 140 concludes whether a ventricular event is sensed. If a ventricular event is sensed by the ventricular sensing unit 130 using any of the electrode pairs, the operation returns back to step S1 to start a new AEI.

However, if no ventricular event is sensed following expiry of the AVI in step S10, the controller 140 controls the ventricular pulse generator 130 to generate a ventricular stimulating pulse that is delivered to the ventricle in step S11.

Following generation of the ventricular stimulating pulse in step S11, the controller 140 triggers the evoked response detector 133 to start sensing in step S12 for any evoked response of the ventricle in response to the delivered ventricular stimulating pulse. If the evoked response detector 133 detects an evoked response the operation continues back to step S1, where a new AEI is started and the operation of the IMD continues for the next cardiac cycle.

However, if no evoked response is sensed by the evoked response detector 133 following expiry of the defined evoked response time interval, the controller 140 controls the ventricular pulse generator 130 to generate a back-up pulse that is delivered to the ventricle in step S13. The method then continues back to step S1 to start a new cardiac cycle.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. An implantable cardiac stimulating device comprising:
   a lead connector connectable to an atrial lead having at least one electrode and a multi-electrode ventricular lead having at least three spatially separated electrodes along a distal portion of the multi-electrode ventricular lead;
   an atrial pulse generator connected to the lead connector and configured to generate atrial stimulating pulses;
   an atrial sensing unit connected to the lead connector and configured to sense electric events in an atrium of a heart;
   a ventricular pulse generator connected to the lead connector and configured to generate ventricular stimulating pulses;
   a ventricular sensing unit connected to the lead connector and configured to individually sense electric events in a ventricle of the heart using multiple, different pairs of electrodes of the multi-electrode ventricular lead; and
   a controller connected to the atrial pulse generator, the atrial sensing unit, the ventricular pulse generator and the ventricular sensing unit, the controller configured to blank the ventricular sensing unit during a blanking period following delivery of an atrial stimulating pulse by the atrial pulse generator and activate the ventricular sensing unit at expiry of the blanking period to enable the ventricular sensing unit to detect a premature ventricular contraction, PVC, depolarization wave traveling over the ventricle using at least one electrode pair of the multiple, different pairs of electrodes, wherein the PVC depolarization wave is initiated at a ventricular site during the blanking period;
   wherein the multi-electrode ventricular lead is a quadropolar ventricular lead having a first electrode, a second electrode, a third electrode and a fourth electrode; and
   wherein the ventricular sensing unit is configured to individually sense electronic events in the ventricle using a first electrode pair comprising the first electrode and the second electrode, individually sense electronic events in the ventricle using a second electrode pair comprising the second electrode and the third electrode, individually sense electronic events in the ventricle using a third electrode pair comprising the third electrode and the fourth electrode.

2. The implantable cardiac stimulating device according to claim 1, wherein the controller is configured to start an atrioventricular interval from a point of time at which the atrial pulse generator generated an atrial stimulating pulse, and wherein the controller is configured to activate the ventricular sensing unit at expiry of the blanking period to enable the ventricular sensing unit to detect the PVC depolarization wave up to an end of the atrioventricular interval.

3. The implantable cardiac stimulating device according to claim 2, wherein the controller is configured to prevent the ventricular pulse generator from generating a ventricular stimulating pulse at expiry of the atrioventricular interval if the ventricular sensing unit detects the PVC depolarization wave prior expiry of the atrioventricular interval.

4. An implantable cardiac stimulating device comprising:
 a lead connector connectable to an atrial lead having at least one electrode and a multi-electrode ventricular lead having at least three spatially separated electrodes along a distal portion of the multi-electrode ventricular lead;
 an atrial pulse generator connected to the lead connector and configured to generate atrial stimulating pulses;
 an atrial sensing unit connected to the lead connector and configured to sense electric events in an atrium of a heart;
 a ventricular pulse generator connected to the lead connector and configured to generate ventricular stimulating pulses;
 a ventricular sensing unit connected to the lead connector and configured to individually sense electric events in a ventricle of the heart using multiple, different pairs of electrodes of the multi-electrode ventricular lead; and
 a controller connected to the atrial pulse generator, the atrial sensing unit, the ventricular pulse generator and the ventricular sensing unit, the controller configured to blank the ventricular sensing unit during a blanking period following delivery of an atrial stimulating pulse by the atrial pulse generator and activate the ventricular sensing unit at expiry of the blanking period to enable the ventricular sensing unit to detect a premature ventricular contraction, PVC, depolarization wave traveling over the ventricle using at least one electrode pair of the multiple, different pairs of electrodes, wherein the PVC depolarization wave is initiated at a ventricular site during the blanking period;
 wherein the ventricular sensing unit is capable of detecting the PVC depolarization wave using at least two electrode pairs of the multiple, different pairs of electrodes; and
 wherein the controller is configured to calculate a time period from detection of the PVC depolarization wave at a first electrode pair of the at least two electrode pairs to detection of the PVC depolarization wave at a second electrode pair of the at least two electrode pairs and classify the electric event as a PVC if the time period exceeds a threshold time period.

\* \* \* \* \*